(12) United States Patent
Ratakonda et al.

(10) Patent No.: US 10,915,846 B2
(45) Date of Patent: *Feb. 9, 2021

(54) OPTIMIZED MENU PLANNING

(71) Applicant: International Business Machines Corporation, Armonk, NY (US)

(72) Inventors: Krishna C. Ratakonda, Yorktown Heights, NY (US); Lav R. Varshney, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 328 days.

This patent is subject to a terminal disclaimer.

(21) Appl. No.: 14/747,144

(22) Filed: Jun. 23, 2015

(65) Prior Publication Data

US 2015/0371164 A1    Dec. 24, 2015

Related U.S. Application Data

(63) Continuation of application No. 14/565,136, filed on Dec. 9, 2014.

(Continued)

(51) Int. Cl.
*G06Q 10/06* (2012.01)
*A61L 2/16* (2006.01)
(Continued)

(52) U.S. Cl.
CPC ...... *G06Q 10/0637* (2013.01); *A23L 3/34095* (2013.01); *A61L 2/16* (2013.01);
(Continued)

(58) Field of Classification Search
CPC ............... G06Q 10/0637; G06Q 10/06; G06Q 30/0201; B01F 15/00318; G06F 17/30554;
(Continued)

(56) References Cited

U.S. PATENT DOCUMENTS 6,837,148 B1   1/2005   Deschenes et al.
8,200,548 B2*  6/2012   Wiedl ................... G06Q 30/02
                                                    705/26.5

(Continued)

FOREIGN PATENT DOCUMENTS

EP       1389047 B1     7/2009
WO    2013035070 A1     3/2013

OTHER PUBLICATIONS

William Swart, Luca Donno, "Simulation Modeling Improves Operations, Planning, and Productivity of Fast Food Restaurants", Interfaces, vol. 11, No. 6, pp. 35-47, Dec. 1981.

(Continued)

*Primary Examiner* — Florian M Zeender
*Assistant Examiner* — Milena Racic
(74) *Attorney, Agent, or Firm* — Rakesh Roy

(57) ABSTRACT

A method for planning preparation of a plurality of dishes according to a plurality of corresponding recipes includes automatically identifying, by a processor, a plurality of candidate sub-recipes, wherein each candidate sub-recipe in the plurality of candidate sub-recipes comprises an intermediate component that is required by at least two of the plurality of corresponding recipes, and automatically selecting, by the processor, at least one candidate sub-recipe in the plurality of candidate sub-recipes for preparation, in accordance with at least one constraint on the preparation of the plurality of dishes.

16 Claims, 6 Drawing Sheets

Related U.S. Application Data

(60) Provisional application No. 61/913,703, filed on Dec. 9, 2013.

(51) Int. Cl.

| | |
|---|---|
| A23L 3/3409 | (2006.01) |
| G06Q 10/10 | (2012.01) |
| G06F 16/901 | (2019.01) |
| G06F 16/9535 | (2019.01) |
| G06F 16/2457 | (2019.01) |
| G06F 30/00 | (2020.01) |
| G06Q 50/12 | (2012.01) |
| G06F 19/00 | (2018.01) |
| B01F 15/00 | (2006.01) |
| G01N 30/88 | (2006.01) |
| G06F 17/11 | (2006.01) |
| G06F 17/16 | (2006.01) |
| G16H 20/60 | (2018.01) |
| G16H 10/20 | (2018.01) |
| G09B 19/00 | (2006.01) |
| G01N 30/02 | (2006.01) |

(52) U.S. Cl.
CPC ....... *B01F 15/00318* (2013.01); *G01N 30/88* (2013.01); *G06F 16/24578* (2019.01); *G06F 16/9024* (2019.01); *G06F 16/9535* (2019.01); *G06F 17/11* (2013.01); *G06F 17/16* (2013.01); *G06F 19/3475* (2013.01); *G06F 30/00* (2020.01); *G06Q 10/063* (2013.01); *G06Q 10/1097* (2013.01); *G06Q 50/12* (2013.01); *G16H 10/20* (2018.01); *G16H 20/60* (2018.01); *A23V 2002/00* (2013.01); *B01D 2257/90* (2013.01); *G01N 2030/025* (2013.01); *G01N 2030/8809* (2013.01); *G09B 19/0092* (2013.01)

(58) Field of Classification Search
CPC . G06F 17/30663; G06F 17/3071; G06F 17/30
See application file for complete search history.

(56) References Cited

U.S. PATENT DOCUMENTS

| | | | | |
|---|---|---|---|---|
| 8,615,530 | B1 | 12/2013 | LeTourneau | |
| 9,165,320 | B1* | 10/2015 | Belvin | G06Q 30/0633 |
| 9,536,237 | B2* | 1/2017 | Argue | G06Q 30/0633 |
| 9,576,034 | B2* | 2/2017 | Kamei | G06Q 50/04 |
| 9,600,793 | B2 | 3/2017 | Varshney | |
| 9,740,998 | B2* | 8/2017 | Cartwright | H04L 67/10 |
| 2002/0046060 | A1 | 4/2002 | Hoskyns et al. | |
| 2002/0099589 | A1* | 7/2002 | Rice | G06Q 10/06311 705/7.14 |
| 2003/0195779 | A1* | 10/2003 | Scholl | G06Q 10/06 702/19 |
| 2003/0225731 | A1 | 12/2003 | Vidgen | |
| 2005/0048186 | A1 | 3/2005 | Lehmberg | |
| 2005/0060332 | A1* | 3/2005 | Bernstein | G06F 16/86 |
| 2006/0053122 | A1* | 3/2006 | Korn | G06F 16/84 |
| 2006/0129582 | A1* | 6/2006 | Schiffmann | G06F 16/2246 |
| 2009/0037288 | A1* | 2/2009 | Christensen | G06F 17/30 705/26.8 |
| 2009/0234712 | A1 | 9/2009 | Kolawa et al. | |
| 2009/0311403 | A1 | 12/2009 | Grab | |
| 2010/0265059 | A1 | 10/2010 | Melker | |
| 2012/0136751 | A1* | 5/2012 | Ochtel | G06Q 30/0633 705/26.8 |
| 2013/0149679 | A1 | 6/2013 | Tokuda | |
| 2013/0224694 | A1 | 8/2013 | Moore et al. | |
| 2015/0032727 | A1* | 1/2015 | Chung | G06Q 30/0251 707/722 |
| 2015/0066386 | A1 | 3/2015 | Varshney | |
| 2015/0161748 | A1 | 6/2015 | Ratakonda | |

OTHER PUBLICATIONS

Manjari Gupta, Akshara Pande, "Design Patterns Mining using Subgraph Isomorphism: Relational View", International Journal of Software Engineering and Its Applications, vol. 5, No. 2, pp. 47-56, Apr. 2011.

W. Burger, M. Burge, and W. Mayr, "Learning to recognize generic visual categories using a hybrid structural approach", in Proc. IEEE Int. Conf. Image Proc., pp. 321-324, Sep. 1996.

B.T. Messmer, H. Bunke, "A new algorithm for error-tolerant subgraph isomorphism detection", IEEE Transactions on Pattern Analysis and Machine Intelligence, vol. 20, No. 5, pp. 493-504, May 1998.

B.T. Messmer, H. Bunke, "Efficient subgraph isomorphism detection: a decomposition approach", IEEE Transactions on Knowledge and Data Engineering, vol. 12, No. 2, pp. 307-323, Mar./Apr. 2000.

Richard G. Morris, et al., "Soup Over Bean of Pure Joy: Culinary Ruminations of an Artificial Chef", International Conference on Computational Creativity, pp. 119-125, 2012.

Michelle M. Cox, Richard Fox, "The Application of a Generic Task Routine Decision Making Algorithm to Recipe Selection in Meal Planning", Department of Computer Science, The University of Texas-Pan American, Oct. 2002.

IBM: List of IBM Patents or Patent Applications Treated as Related (Appendix P), Sep. 26, 2019, pp. 1-2.

Ahn et al., "Flavor network and the principles of food pairing," Scientific Reports, vol. 1: 196, Dec. 2011, 7 pages.

International Search Report and Written Opinion of International Application No. PCT/US2014/69108 dated Mar. 10, 2015, pp. 1-8.

IBM: List of IBM Patents or Patent Applications Treated as Related (Appendix P), Jul. 28, 2020, pp. 1-2.

* cited by examiner

OPTIMIZED MENU PLANNING

FIELD OF THE DISCLOSURE

This disclosure relates generally to the field of food preparation, and relates more specifically to the use of analytics to optimize food preparation in a manner that reduces preparation time and inventory carrying costs.

BACKGROUND OF THE DISCLOSURE

Food preparation, particularly in a commercial setting such as a restaurant or food processing plant, may involve the simultaneous or near-simultaneous preparation of multiple dishes (i.e., sets of ingredients prepared according to respective recipes). These dishes may or may not be the same, and the queue of dishes to be prepared may change dynamically. Moreover, there may be limits on the amount of time that can be taken to prepare the dishes.

Preparation of food is associated with various costs, including the time required to prepare the food and the carrying costs required to hold the inventory necessary to prepare the food (e.g., the ingredients, the facilities/equipment, etc.). It is desirable, especially commercial food preparation settings, to minimize these costs.

SUMMARY OF THE DISCLOSURE

A method for planning preparation of a plurality of dishes according to a plurality of corresponding recipes includes automatically identifying, by a processor, a plurality of candidate sub-recipes, wherein each candidate sub-recipe in the plurality of candidate sub-recipes comprises an intermediate component that is required by at least two of the plurality of corresponding recipes, and automatically selecting, by the processor, at least one candidate sub-recipe in the plurality of candidate sub-recipes for preparation, in accordance with at least one constraint on the preparation of the plurality of dishes.

In another embodiment, the present disclosure provides a device for planning preparation of a plurality of dishes according to a plurality of corresponding recipes. The device includes a processor and a computer-readable medium storing instructions which, when executed by the processor, cause the processor to perform operations including: identifying, by a processor, a plurality of candidate sub-recipes, wherein each candidate sub-recipe in the plurality of candidate sub-recipes comprises an intermediate component that is required by at least two of the plurality of corresponding recipes, and selecting, by the processor, at least one candidate sub-recipe in the plurality of candidate sub-recipes for preparation, in accordance with at least one constraint on the preparation of the plurality of dishes.

In another embodiment, the present disclosure provides system for planning preparation of a plurality of dishes according to a plurality of corresponding recipes. The system includes a database storing the plurality of corresponding recipes and an application server for identifying a plurality of candidate sub-recipes, wherein each candidate sub-recipe in the plurality of candidate sub-recipes comprises an intermediate component that is required by at least two of the plurality of corresponding recipes, and for selecting at least one candidate sub-recipe in the plurality of candidate sub-recipes for preparation, in accordance with at least one constraint on the preparation of the plurality of dishes.

BRIEF DESCRIPTION OF THE DRAWINGS

The teachings of the present disclosure can be readily understood by considering the following detailed description in conjunction with the accompanying drawings, in which.

DETAILED DESCRIPTION

Figure 1:
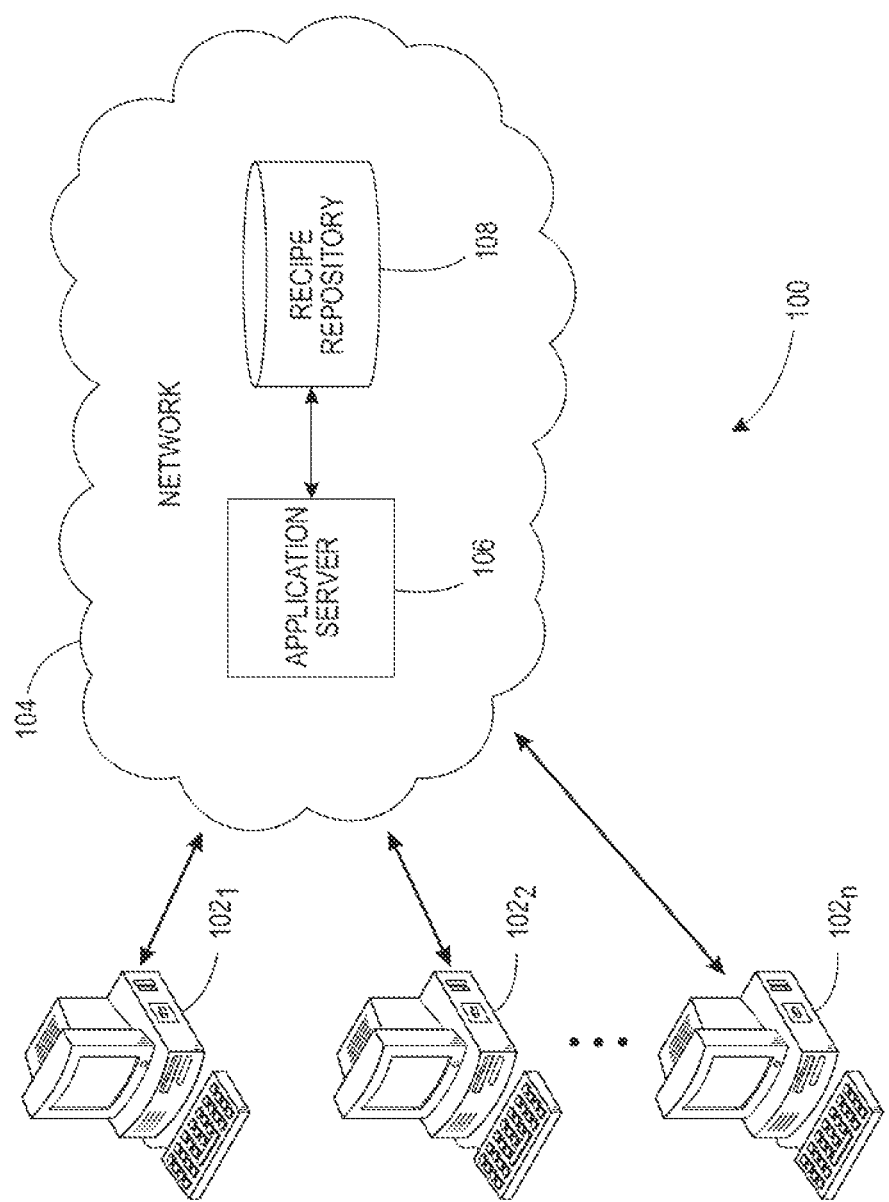
FIG. 1 illustrates one embodiment of a system for optimized menu planning, according to the present disclosure.

In one embodiment, the present disclosure is related to a method and apparatus for optimized menu planning. For example, one embodiment of the present disclosure assumes that the recipe for each dish in a menu (i.e., a set of dishes to be prepared) can be broken down into a plurality of "sub-recipes" that can be prepared independently (with some restrictions and dependencies imposed by the recipe). The results of the sub-recipes can subsequently be combined to form the dish. There may be multiple ways in which a single recipe can be broken down into sub-recipes.

Further embodiments of the disclosure assume that several dishes in a menu share common sub-recipes. Thus, if a sub-recipe is common across multiple dishes in a menu, the quantities of the sub-recipe required by the multiple dishes may be pooled to form an aggregate amount of the sub-recipe that can be prepared at one time (and subsequently divided among the multiple dishes as needed). Thus, embodiments of the disclosure assume that it is more efficient, from both a cost and time perspective, to prepare a single larger quantity of a sub-recipe than it is to prepare multiple smaller quantities of the same sub-recipe (assuming equal carrying costs and wastage).

Thus, given: (1) a repository of recipes for dishes; (2) a prioritized queue of pending requests for dishes and the stochastic likelihood of new requests for dishes being received during a given time period; and (3) constraints on one or more of: worker availability, quantity and type of equipment available, quantity and type of ingredients available, and timing restrictions imposed by the recipes, embodiments of the disclosure identify the sub-recipes (including quantity) that should be prepared at one or more instances of time to maximize an objective function that balances on-time delivery of dishes with wastage and other costs. Embodiments of the disclosure therefore jointly minimize the time taken and the inventory carrying costs associated with preparing a menu.

One aspect of the present disclosure is to modify a function of a computer based on specific dishes that are to be prepared in a food preparation setting and/or on historical food consumption patterns for the setting. For instance, the computer may identify optimal sub-recipes (and their quantities) for preparation in aggregate based on the types, priorities, or historical consumption patterns of the dishes to be prepared. Notably, a machine is required to modify certain portions of the computer as candidate sub-recipes are identified, ranked, and selected for preparation.

Embodiments of the present disclosure transform a set of disparate recipes and constraints into a suggested set of optimal sub-recipes that can be prepared in aggregate and shared among two or more of the recipes. In other words, a set of recipes does not typically dictate how or when specific components of a given recipe may be prepared in aggregate and shared with specific other recipes. However, embodiments of the present disclosure take a set of disparate recipes and transform it into a set of optimal sub-recipes (and their quantities). Although some of the recipes and/or constraints may be supplied by a human user, the transformation of the recipes into the suggested optimal sub-recipes is performed with little or no human assistance (i.e., automatically).

A "recipe" as used herein refers to a set of instructions for preparing a dish (i.e., food item), including the ingredients and quantities of ingredients. A "sub-recipe" is thus the set of instructions (including ingredients and quantities) for preparing an intermediate component of the dish. For instance, if one has a recipe for lasagna, the recipe might be broken into separate sub-recipes for preparing the noodles, the sauce, and the cheese. The noodles, sauce, and cheese, once prepared individually, may then be combined to form the lasagna. Moreover, as discussed above, the sub-recipes for the sauce and the cheese might also be usable to form intermediate components of other dishes (e.g., manicotti).

FIG. 1 illustrates one embodiment of a system 100 for optimized menu planning, according to the present disclosure. The system 100 generally comprises one or more endpoint devices $102_1$-$102_n$. (hereinafter collectively referred to as endpoint devices 102") coupled to a network 104. The network 104, in turn, generally comprises an application server 106 and one or more databases $108_1$-$108_m$ (hereinafter collectively referred to as "databases 108").

The network 104 is a communications network. The network 104 may be any type of communications network, such as for example, a traditional circuit switched network (e.g., a public switched telephone network (PSTN)) or an Internet Protocol (IP) network (e.g., an IP Multimedia Subsystem (IMS) network, an asynchronous transfer mode (ATM) network, a wireless network, a cellular network (e.g., 2G, 3G and the like), a long term evolution (LTE) network, and the like) related to the current disclosure. It should be noted that an IP network is broadly defined as a network that uses Internet Protocol to exchange data packets. Additional exemplary IP networks include Voice over IP (VoIP) networks, Service over IP (SoIP) networks, and the like.

In one embodiment, the network 104 may comprise a core network that is in communication with one or more access networks (not shown), where the access networks may include a wireless access network (e.g., a WiFi network and the like), a cellular access network, a PSTN access network, a cable access network, a wired access network and the like. In one embodiment, the access networks may all be different types of access networks, may all be the same type of access network, or some access networks may be the same type of access network and other may be different types of access networks. The core network and the access networks may be operated by different service providers, the same service provider or a combination thereof.

As discussed above, the network 104 includes an application server 106 and one or more databases 108. Although only a single application server 106 and a single database 108 are illustrated, it should be noted that any number of application servers 106 or databases 108 may be deployed.

Figure 6:
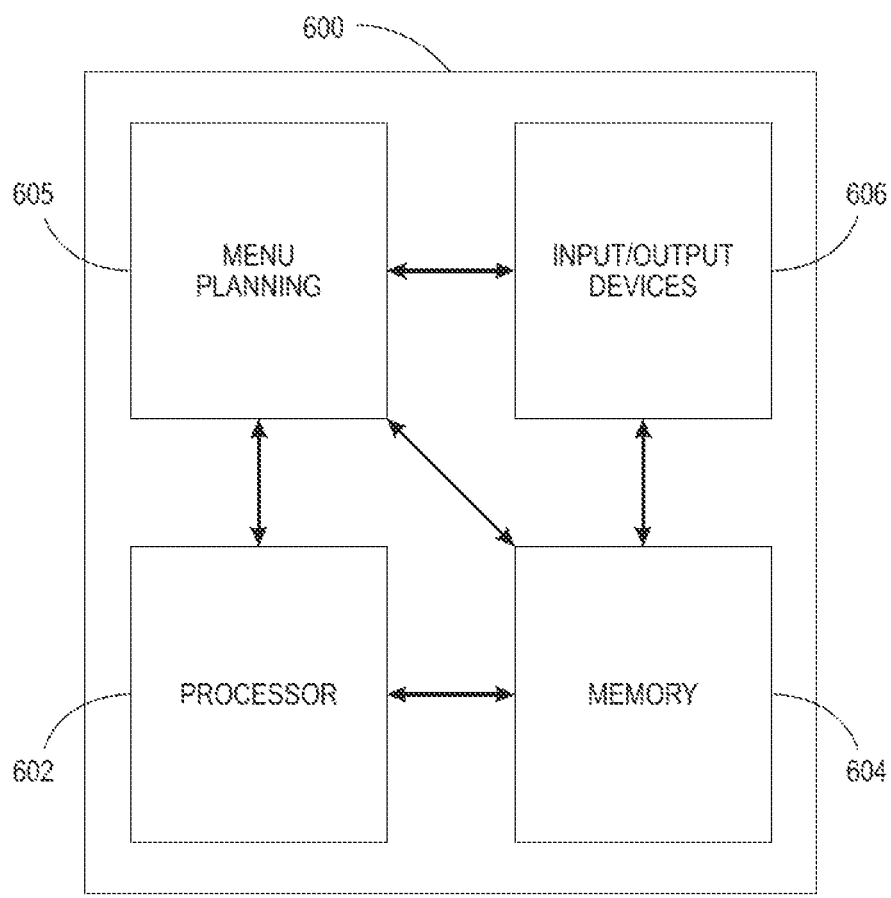
FIG. 6 is a high-level block diagram of a general purpose computing device suitable for use in performing the functions described herein.

One embodiment of an application server 106 is described in greater detail in connection with FIG. 2. In another embodiment, the application server 106 may comprise a general purpose computer configured as a special purpose computer, as illustrated in FIG. 6 and discussed below. In one embodiment, the application server 106 may perform the methods and algorithms discussed below related to optimized menu planning. For instance, the application server 106 may suggest one or more sub-recipes that may be prepared in response to a set of inputs (received from the endpoint devices 102 and/or database 108, for example) including dishes to be prepared, recipes for the dishes, and constraints on the preparation of the dishes.

In one embodiment, the database 108 is a repository of recipes for a plurality of dishes. In a further embodiment, the database 108 may additionally store sub-recipes associated with these recipes, which may aid in more efficiently identifying sub-recipes that are common across multiple disparate recipes, as well as the quantities of each sub-recipe that are needed. In one embodiment, the database 108 may additionally store data regarding the historical consumption patterns of various dishes.

In one embodiment, the network 104 is in communication with the endpoint devices 102. In one embodiment, the endpoint devices 102 may be any type of computing device such as a desktop computer, a tablet computer, a laptop computer, a netbook, an ultrabook, a cellular telephone, a smart phone, a portable media device (e.g., an MP3 player), a gaming console, a portable gaming device, and the like. It should be noted that although only three endpoint devices 102 are illustrated in FIG. 1, any number of endpoint devices 102 may be deployed.

In an alternative embodiment, the methods performed by the application server 106 may be performed locally by the endpoint devices 102. In this case, the endpoint devices 102 access the databases 108 directly over the network 104 and perform the methods and algorithms discussed below related to planning a menu.

It should be noted that the network 104 has been simplified. For example, the network 104 may include other network elements (not shown) such as border elements, routers, switches, policy servers, security devices, a content distribution network (CDN) and the like.

Figure 2:
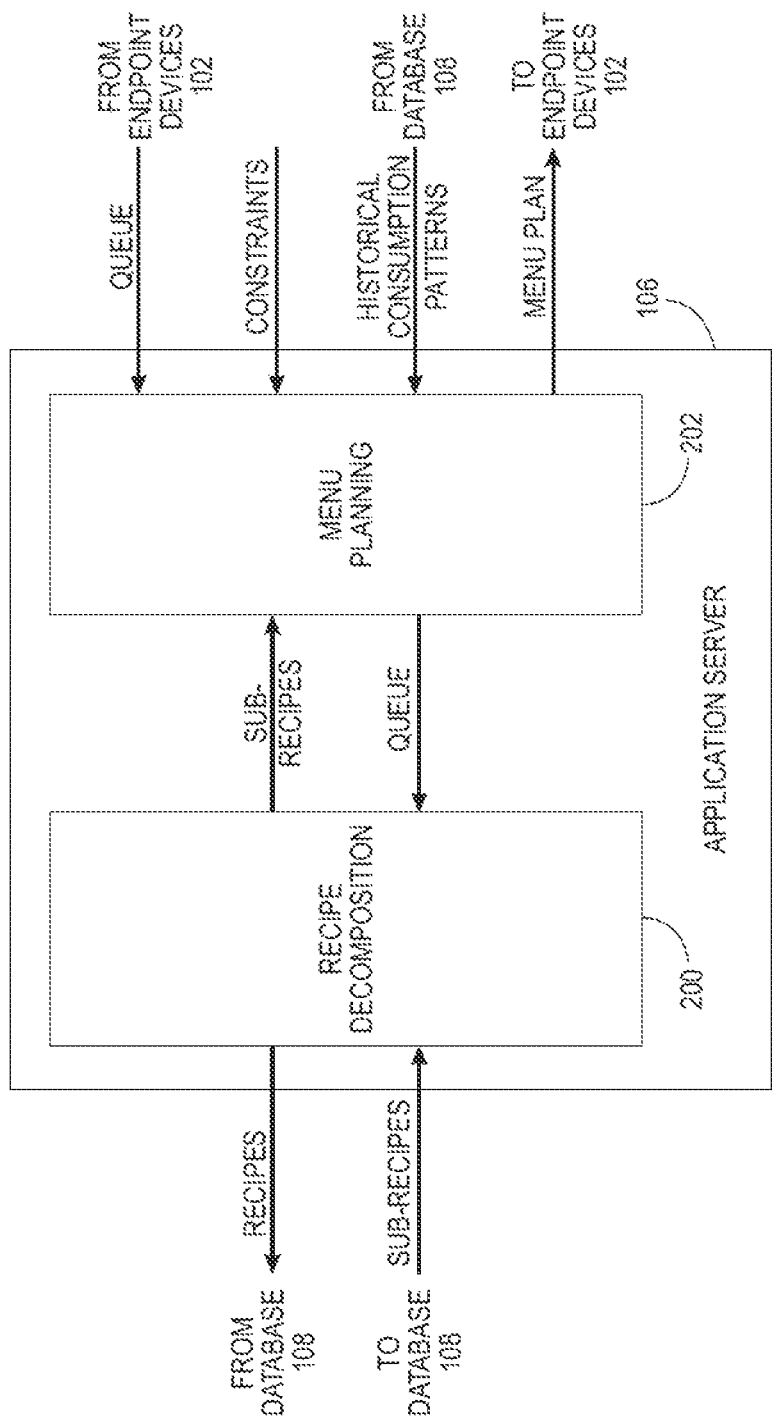
FIG. 2 is a block diagram illustrating the application server of FIG. 1 in greater detail.

FIG. 2 is a block diagram illustrating the application server 106 of FIG. 1 in greater detail. In general, the application server 106 receives a plurality of inputs from endpoint devices 102. The plurality of inputs relate to a menu to be planned, and may include, for example, a queue of dishes to be prepared and one or more constraints on preparation of the dishes. The application server 106 produces as output a suggested set of optimal sub-recipes responsive to the plurality of inputs. The suggested set of optimal sub-recipes may be incorporated into a menu plan including a set of scheduled tasks, allocated among the available resources, for preparing the dishes in the queue, potentially with some flexibility built in to accommodate new requests for dishes not included in the queue. Thus, the application server 106 according to embodiments of the present disclosure transforms a set of criteria (e.g., requested dishes, available resources, etc.) into a suggested set of optimal sub-recipes (e.g., intermediate components of the requested dishes that can be prepared in aggregate to make the most efficient use of the available resources).

As illustrated, the application server 106 generally comprises a recipe decomposition engine 200 and a menu planning engine 202. Either or both of the recipe decomposition engine 200 and the menu planning engine 202 may be implemented as a processor.

The recipe decomposition engine 200 obtains as inputs a plurality of recipes. These recipes may be obtained, for example, from the database 108. The recipe decomposition engine 200 breaks one or more of these recipes down into a plurality of sub-recipes, as discussed above. A given recipe may have more than one way of being broken down into sub-recipes. Moreover, a given sub-recipe may be shared by multiple recipes.

Figure 3:
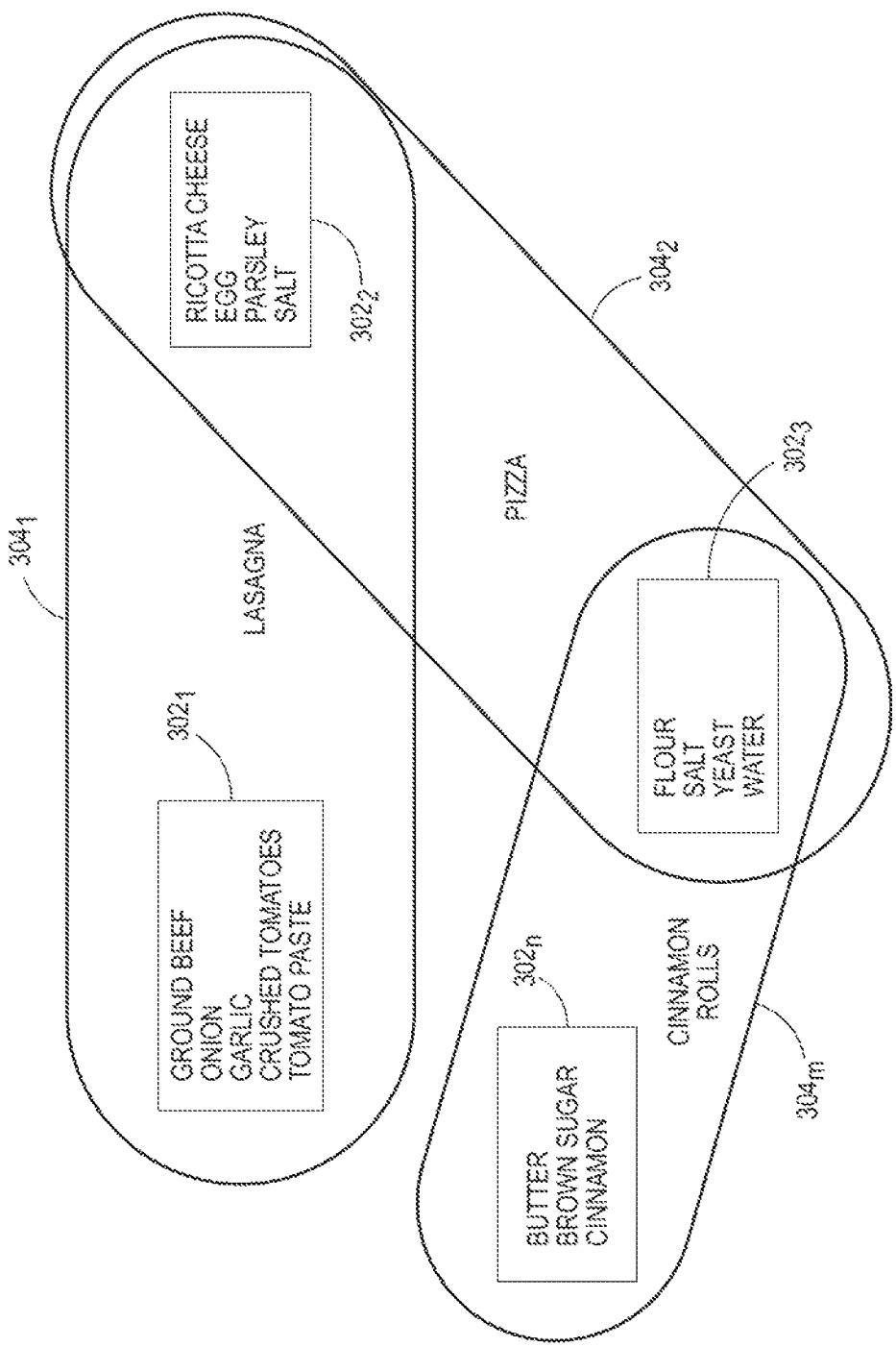
FIG. 3 illustrates a plurality of exemplary sub-recipes.

FIG. 3, for instance, illustrates a plurality of exemplary sub-recipes $302_1$-$302_n$. (hereinafter collectively referred to as "sub-recipes 302"). The sub-recipes have been simplified for the purposes of illustration; only the ingredients, and not the amounts or steps used to prepare the ingredients, are depicted. Each of the sub-recipes 302 may form an intermediate component of multiple different recipes $304_1$-$304_m$ (hereinafter collectively referred to as "recipes 304"). Again, the recipes have been simplified for the purposes of illustration; only the names of the dishes, and not the full sets of ingredients, amounts, and steps, are depicted. As an example, the sub-recipe $302_2$ that combines ricotta cheese, eggs, parsley, and salt in specific proportions may be used in the recipes for both lasagna $304_1$ and pizza $304_2$. Thus, if the lasagna recipe requires eight ounces of this sub-recipe, and the pizza recipe requires six ounces of this sub-recipe, at least fourteen ounces of the sub-recipe may be prepared at once, and then allocated as needed among the lasagna and pizza recipes.

The recipe decomposition engine 200 may optionally store the sub-recipes in the database 108, where the sub-recipes may be indexed according to the recipes to which they correspond. The index may be annotated with the quantities of the sub-recipe that are required by each of the corresponding recipes.

Figure 4:
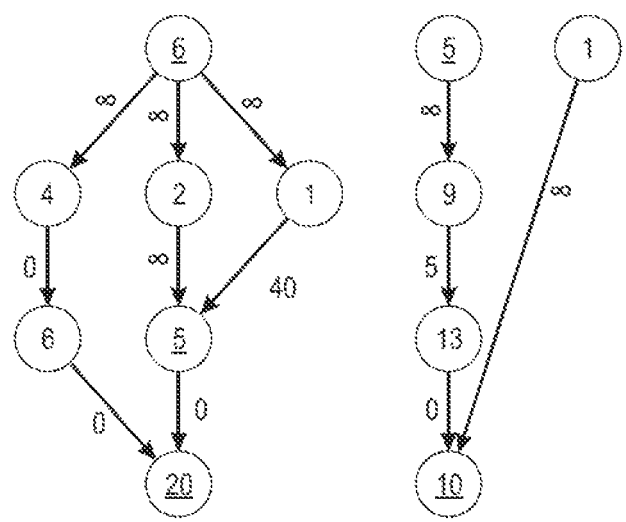
FIG. 4 depicts two exemplary recipes modeled as directed acyclic graphs.

The recipes themselves may be represented in the database 108 as directed acyclic graphs. FIG. 4, for example, depicts two exemplary recipes modeled as directed acyclic graphs. In this case, the nodes of the graphs represent steps of the recipes (e.g., boil the water); labels of the nodes indicate the duration of the corresponding step (e.g., in minutes). Edges between nodes indicate an order in which certain steps are to be performed; some steps may be dependent upon other steps being completed first (e.g., pasta cannot be put into water until the water has first been boiled). Labels of the edges indicate the maximum amount of time (e.g., in minutes) that can elapse between two sequential steps. If an edge is labeled with an infinite amount of time (or another relatively large period of time), then the edge can be cut to partition the recipe into sub-recipes.

The menu planning engine 202 may obtain the sub-recipes directly from the recipe decomposition engine 200 or from the database 108. In addition, the menu planning engine 202 obtains a plurality of inputs. One of these inputs is a queue of dishes to be prepared (i.e., pending requests for dishes). The queue may optionally be prioritized in a manner that specifies which dishes in the queue should be prepared first. Additional inputs may include constraints on the preparation of dishes in the queue. These constraints may include, for example: worker availability, quantity and type of available equipment, quantity and type of available ingredients, and/or timing restrictions imposed by the recipes for the dishes in the queue. Based on these inputs and on the sub-recipes, the menu planning engine 202 generates a suggested set of optimal sub-dishes that can be prepared to facilitate preparation of the dishes in the queue in the most efficient manner possible, subject to the constraints. In one embodiment, discussed in further detail below, the menu planning engine 202 generates the suggested set of optimal sub-dishes by maximizing an objective function that balances the on-time delivery of the dishes in the queue with wastage and other costs. The objective function may also consider the stochastic likelihood of new requests for dishes being received.

In one embodiment, generation of the suggested set of optimal sub-dishes involves determining three major items based on the inputs: (1) a candidate set of common sub-recipes that can be prepared "in bulk;" (2) an optimal amount of each sub-recipe that should be pre-prepared to attain a balance between on-time delivery of dishes and inventory carrying costs; and (3) an optimal amount of each sub-recipe that should be pre-prepared to minimize expected queue length by balancing the cost of preparing more of the sub-recipe to satisfy future queue items versus the cost of delaying delivery of items currently in the queue.

Figure 5:
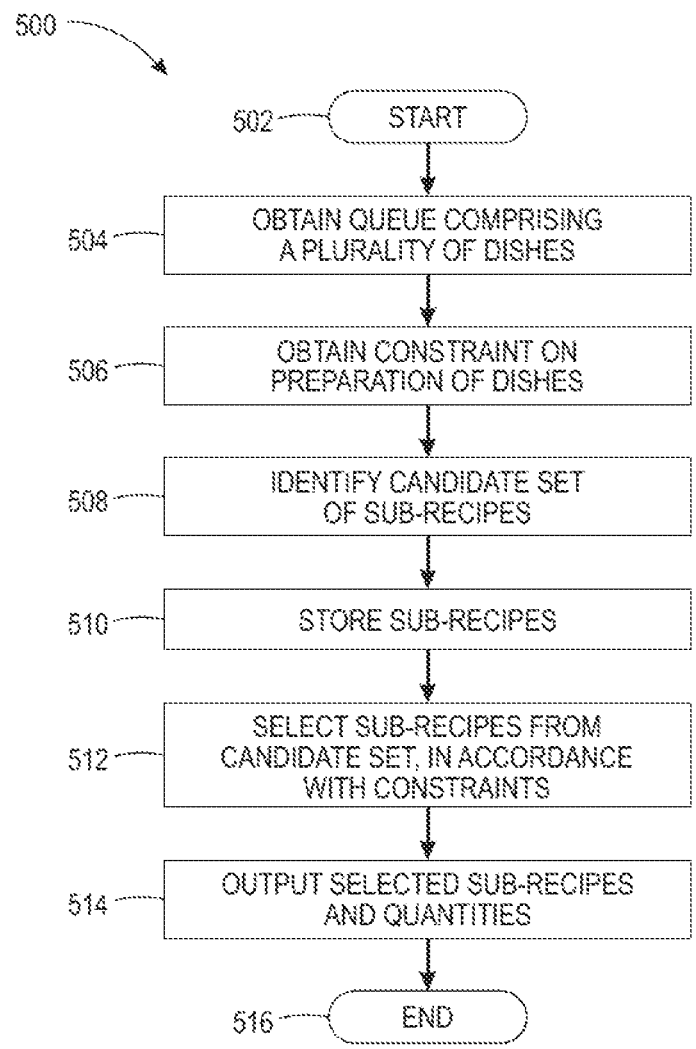
FIG. 5 is a flow diagram illustrating the high level method for planning a menu, according to embodiments of the present disclosure.

FIG. 5 is a flow diagram illustrating the high level method 500 for planning a menu, according to embodiments of the present disclosure. The method 500 may be performed, for example, by the application server 106 illustrated in FIGS. 1 and 2 and described in detail above. However, it will be appreciated that the method 500 is not limited to implementation on the application server 106; in alternate embodiments, the method 500 may be performed by other devices or systems, including the endpoint devices 102 or a general purpose computing device that is configured as a special purpose computing device.

The method 500 begins in step 502.

In step 504, the menu planning engine 202 obtains a queue comprising a series of dishes to be prepared. The queue also includes the quantities of each dish that are needed, and the time at which each dish is expected to be delivered. For instance, the queue may be a series of orders for meals to be prepared by a restaurant kitchen staff. The queue may optionally be prioritized to indicate which dishes should be prepared first. For instance, a first-in-first-out prioritization scheme may be employed in which the dishes are prepared in the order that they enter the queue. Alternatively, dishes that require greater preparation time may be started sooner, so that they may be delivered simultaneously with dishes that require less preparation time and are to be delivered to the same party. Other prioritization schemes also are possible in this step.

In step optional 506 (illustrated in phantom), the menu planning engine 202 obtains one or more constraints on the preparation of dishes in the queue. These constraints may include, for example: worker availability, quantity and type of available equipment, quantity and type of available ingredients, and/or timing restrictions imposed by the recipes for the dishes in the queue.

In step 508, the recipe decomposition engine 200 identifies a candidate set of sub-recipes, from among the recipes for the dishes in the queue. In particular, the recipe decomposition engine 200 identifies sub-recipes that are shared by two or more of the dishes in the queue, such that the amounts of the sub-recipe required by the dishes may be prepared together as a single quantity and that is subsequently divided as needed among the dishes. In order to be a candidate for inclusion in the set of sub-recipes, the two or more dishes that require the sub-recipe must require the same ingredients in the same proportions and prepared in the same sequence of steps. Furthermore, some recipes may be more specific than others in terms of ingredients or instructions (e.g., "salt" versus "Celtic salt"), and these more specific ingredients and instructions must also be taken into account in determining the set of candidate sub-recipes. In addition, some recipes may place a time limit on the use of the sub-recipe output, and such time limits must also be considered in step 508. In one embodiment, sub-recipes may be ranked or scored for suitability, for example according to an error tolerance in the corresponding recipes and/or another fitness measure.

The recipes may be retrieved from the database 108, which may store representations of the recipes as directed acyclic graphs, as discussed above. In this case, step 508 may be posed as a problem of finding subgraph isomorphisms in a collection of directed acyclic graphs, where the directed acyclic graphs represent the complete recipes, and the subgraph isomorphisms represent the candidate sub-recipes.

In optional step 510, the sub-recipes are stored, for example in the database 108.

In step 512, the menu planning engine 202 generates a list of sub-recipes that are selected for preparation, along with the quantities of each sub-recipe that are to be prepared. Selection of the sub-recipes is based at least in part on the prioritization of the dishes in the queue and/or on the optional constraints. The quantity of a given sub-recipe that is required is at least the sum of the quantities of the given sub-recipe that are required by two or more of the recipes for dishes in the queue.

In addition, sub-recipes may be selected to account for the addition of expected new dishes to the queue (e.g., the stochastic likelihood of new requests for dishes being received during a given time period). For instance, historical usage patterns may indicate a likelihood of the level of consumption of various dishes. This information may aid in determining an optimal amount of a sub-recipe that should be pre-prepared in order to attain a balance between on-time delivery of dishes in the queue and inventory carrying costs (e.g., waste of perishable ingredients, preservation costs, etc.). In one embodiment, the menu planning engine 202 evaluates this problem as a minimization of an appropriately weighted objective function that has three elements: (1) a penalty function for delays (e.g., lost business); (2) a resource cost (e.g., human and/or equipment); and (3) an inventory carrying cost. The penalty cost and the inventory carrying cost are stochastic in nature.

Alternatively or in addition, historical usage patterns may be used to determine an optimal amount of sub-recipe that can be pre-prepared in order to minimize the expected future length of the queue (e.g., average or maximum length). In this case, inventory carrying costs and resource costs are assumed to be sunk costs, and the costs to be balanced by the weighted objective function are the cost of satisfying an existing item in the queue versus the cost of preparing more of the sub-recipe (and thus delaying satisfaction of the existing item in order to ensure that many more future orders can be satisfied in a timely manner). In one embodiment, this is posed as a dynamic programming problem with an appropriate cost function.

In step 514, the menu planning engine outputs the selected sub-recipes, along with the quantities of the selected sub-recipes that are to be prepared. The menu planning engine 514 may output this data to the endpoint devices 102, or may output the data to another machine or process that generates a more detailed menu plan for preparing all of the dishes in the queue.

The method 500 ends in step 516.

FIG. 6 depicts a high-level block diagram of a general-purpose computer suitable for use in performing the functions described herein. As depicted in FIG. 6, the system 600 comprises a hardware processor element 602 (e.g., a central processing unit (CPU), a microprocessor, or a multi-core processor), a memory 604, e.g., random access memory (RAM) and/or read only memory (ROM), a module 605 for planning a menu, and various input/output devices 606 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the respective systems and/or methods discussed above can be used to configure a hardware processor to perform the steps functions and/or operations of the above disclosed systems and methods. In one embodiment, instructions and data for the present module or process 605 for planning a menu (e.g., a software program comprising computer-executable instructions) can be loaded into memory 604 and executed by hardware processor element 602 to implement the steps, functions or operations as discussed above in connection with the exemplary systems 100 and 106 and/or method 500. The processor executing the computer readable or software instructions relating to the above described method(s) can be perceived as a programmed processor or a specialized processor. As such, the present module 605 for planning a menu (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

Referring to FIG. 6, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A device comprising:
 a processor; and
 a non-transitory computer-readable medium storing instructions which, when executed by the processor, cause the processor to perform operations, the operations comprising:
 receiving, by a processor, a plurality of data packets from an endpoint device;

extracting, by the processor, a plurality of dishes from the plurality of data packets;

retrieving, by the processor, a plurality of disparate recipes in electronic form from an electronic database, wherein the plurality of disparate recipes describe how to prepare the plurality of dishes;

modeling, by the processor, the plurality of disparate recipes as a plurality of directed acyclic graphs, where nodes of the plurality of directed acyclic graphs represent steps of the plurality of disparate recipes, labels of the nodes indicate durations of the steps, edges between the nodes indicate an order in which the steps are to be performed, and labels of the edges indicate maximum amounts of time that can elapse between two sequential steps;

determining a sub-recipe based on identifying, by the processor, a subgraph isomorphism in the plurality of directed acyclic graphs, wherein the subgraph isomorphism represents the sub-recipe that appears in at least two disparate recipes of the plurality of disparate recipes, wherein the sub-recipe comprises a specific sequence of steps for combining a specific plurality of ingredients in specific proportions, such that each recipe of the at least two disparate recipes include the same specific plurality of ingredients combined in the same specific proportions according to the same specific sequence of steps;

automatically generating, by the processor, a preparation schedule for the plurality of dishes, wherein the preparation schedule includes preparing the sub-recipe in bulk in a quantity that is at least a sum of respective quantities of the sub-recipe contained in each recipe of the at least two disparate recipes, wherein the preparation schedule respects at least one constraint on the preparation of the plurality of dishes;

storing, by the processor, the sub-recipe in the electronic database;

indexing the sub-recipe in the electronic database according to the at least two disparate recipes of the plurality of disparate recipes, wherein the indexing includes annotating the sub-recipe with the respective quantities of the sub-recipe that are included in the at least two disparate recipes of the plurality of disparate recipes; and in response to searching the electronic database for the sub-recipe, locating the at least two disparate recipes of the plurality of disparate recipes corresponding to the sub-recipe, wherein each located recipe of the at least two disparate recipes is annotated with the respective quantities of the sub-recipe.

2. The device of claim 1, wherein the constraint is a quantity of each of the plurality of dishes that is required.

3. The device of claim 1, wherein the constraint is a time at which at least one of the plurality of dishes is required to be delivered.

4. The device of claim 1, wherein the constraint is a prioritization of the plurality of dishes.

5. The device of claim 1, wherein the constraint is an availability of equipment required to prepare at least one of the plurality of dishes.

6. The device of claim 1, wherein the constraint is an availability of a worker required to prepare at least one of the plurality of dishes.

7. The device of claim 1, wherein the constraint is a timing restriction imposed by one of the plurality of disparate recipes.

8. The device of claim 1, wherein the constraint is a time limit on the use of an intermediate component that is a result of the sub-recipe by one of the at least two disparate recipes.

9. The device of claim 1, wherein the constraint is an expected addition of a new dish to the plurality of dishes.

10. The device of claim 9, wherein the expected addition is estimated based on an historical usage pattern of the new dish.

11. The device of claim 1, further comprising:
automatically ranking the sub-recipe relative to other sub-recipes of a plurality of sub-recipes, prior to the automatically generating.

12. The device of claim 11, wherein the ranking is based on an error tolerance in the plurality of disparate recipes.

13. The device of claim 1, wherein the preparation schedule further balances the on-time delivery of the plurality of dishes versus at least one cost of preparing the plurality of dishes.

14. The device of claim 13, wherein the at least one cost is an inventory carrying cost.

15. A system comprising:
an electronic database storing a plurality of disparate recipes in electronic form; and
an application server
receiving a plurality of data packets from an endpoint device,
extracting a plurality of dishes from the plurality of data packets,
retrieving a subset of the plurality of disparate recipes from the electronic database, wherein the subset of the plurality of disparate recipes describes how to prepare the plurality of dishes,
modeling the subset of the plurality of disparate recipes as a plurality of directed acyclic graphs, where nodes of the plurality of directed acyclic graphs represent steps of the subset of the plurality of disparate recipes, labels of the nodes indicate durations of the steps, edges between the nodes indicate an order in which the steps are to be performed, and labels of the edges indicate maximum amounts of time that can elapse between two sequential steps,
determining a sub-recipe based on identifying a subgraph isomorphism in the plurality of directed acyclic graphs, wherein the subgraph isomorphism represents the sub-recipe that appears in at least two disparate recipes of the plurality of disparate recipes, wherein the sub-recipe comprises a specific sequence of steps for combining a specific plurality of ingredients in specific proportions, such that each recipe of the at least two disparate recipes include the same specific plurality of ingredients combined in the same specific proportions according to the same specific sequence of steps,
generating a preparation schedule for the plurality of dishes that includes preparing the sub-recipe in bulk in a quantity that is at least a sum of respective quantities of the sub-recipe contained in each recipe of the at least two disparate recipes, wherein the preparation schedule respects at least one constraint on the preparation of the plurality of dishes,
storing the sub-recipe in the database,
indexing the sub-recipe in the database according to the at least two disparate recipes of the plurality of disparate recipes, wherein the indexing includes annotating the sub-recipe with the respective quantities of the sub-recipe that are included in the at least two disparate recipes of the plurality of disparate recipes, and in response to searching the electronic database for the sub-recipe, locating the at least two disparate recipes of the plurality of disparate recipes corresponding to the sub-recipe, wherein each located recipe of the at least two disparate recipes is annotated with the respective quantities of the sub-recipe.

16. The system of claim 15, wherein the application is further configured for automatically ranking the sub-recipe relative to other sub-recipes of a plurality of sub-recipes, prior to automatically generating.

* * * * *